United States Patent [19]
Veith

[11] Patent Number: 5,769,851
[45] Date of Patent: Jun. 23, 1998

[54] EXTERNAL FIXATOR

[76] Inventor: Wolfgang Veith, Leisberg 7, D-69124 Heidelberg, Germany

[21] Appl. No.: 839,278

[22] Filed: Apr. 17, 1997

Related U.S. Application Data

[63] Continuation of Ser. No. 519,586, Aug. 25, 1995, abandoned.

[30] Foreign Application Priority Data

Sep. 5, 1994 [DE] Germany .......................... 44 31 525.2
Aug. 5, 1995 [DE] Germany ........................ 195 28 839.4

[51] Int. Cl.[6] .................................................. A61B 17/56
[52] U.S. Cl. .............................................. 606/57; 606/54
[58] Field of Search .................................. 606/53, 54, 55, 606/56, 57, 58, 59, 61; 602/5, 16, 20, 23

[56] References Cited

U.S. PATENT DOCUMENTS

| 2,238,870 | 4/1941 | Haynes | 606/59 |
|---|---|---|---|
| 2,250,417 | 7/1941 | Ettinger | 606/57 |
| 4,620,533 | 11/1986 | Mears | 606/54 |
| 4,923,458 | 5/1990 | Fischer | 606/57 |
| 5,342,360 | 8/1994 | Faccioli et al. | 606/59 |

FOREIGN PATENT DOCUMENTS

| 0 227 594 | 7/1987 | European Pat. Off. . |
|---|---|---|
| 2 457 676 | 12/1980 | France . |
| 2 665 353 | 2/1992 | France . |
| 27 18 515 | 11/1977 | Germany . |
| 27 45 504 | 4/1979 | Germany . |

*Primary Examiner*—Michael Buiz
*Assistant Examiner*—Patrick W. Rasche
*Attorney, Agent, or Firm*—Todd A. Dawson

[57] ABSTRACT

An external fixator or splint with a carrier which carries at least two fastening devices arranged to receive bone screws. The fastening devices are adjustable relative to the carrier and can be locked in various positions by clamping parts. The splint is made up of two ball-and-socket joints which are supported on the carrier so as to be axially adjustable and of two fastening elements that secure the ball-and-sockets joints.

28 Claims, 9 Drawing Sheets

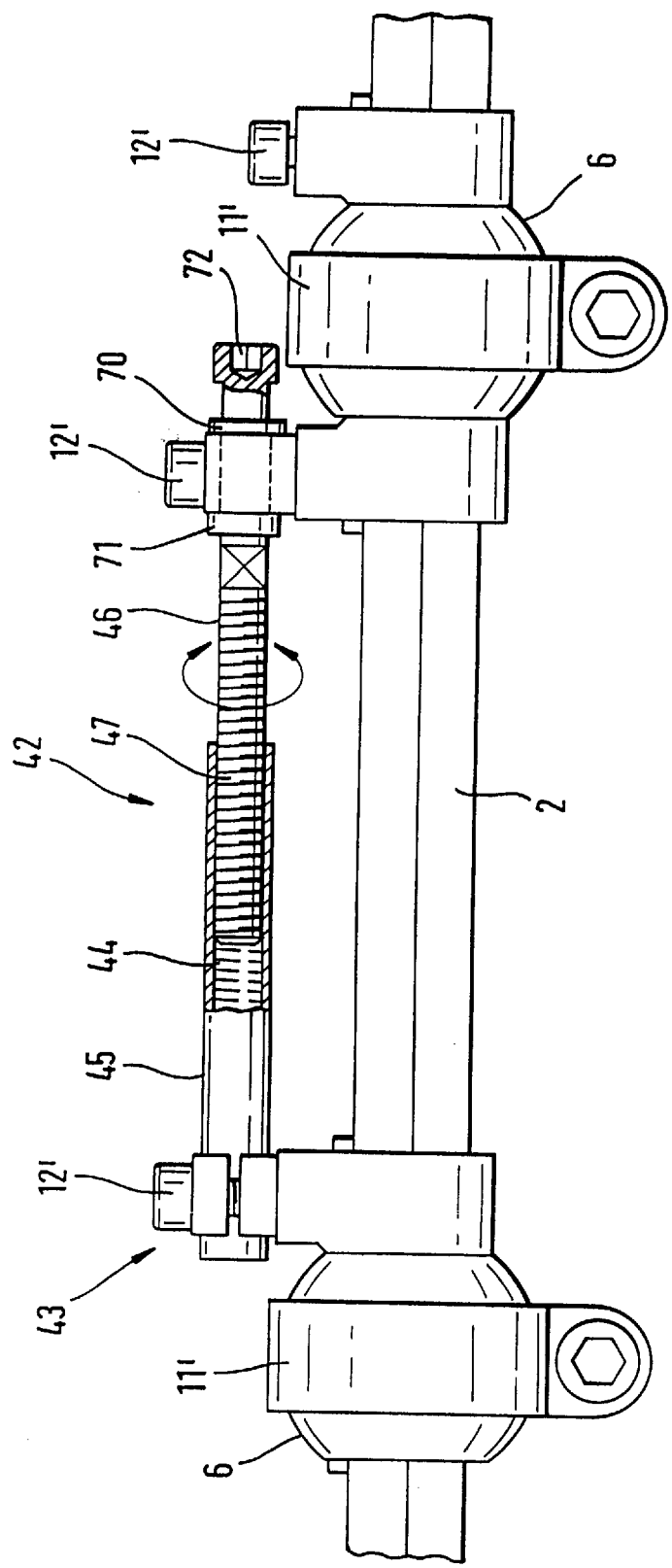
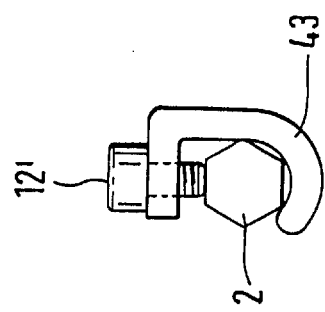
Fig. 14
Fig. 15

Fig. 16
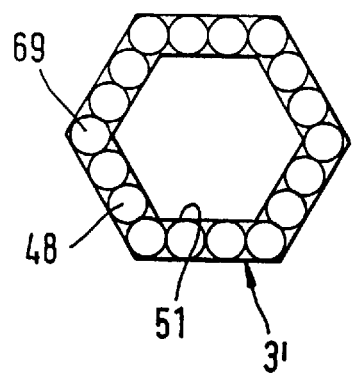
Fig. 17
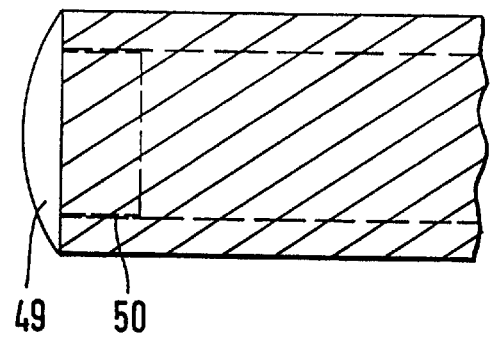
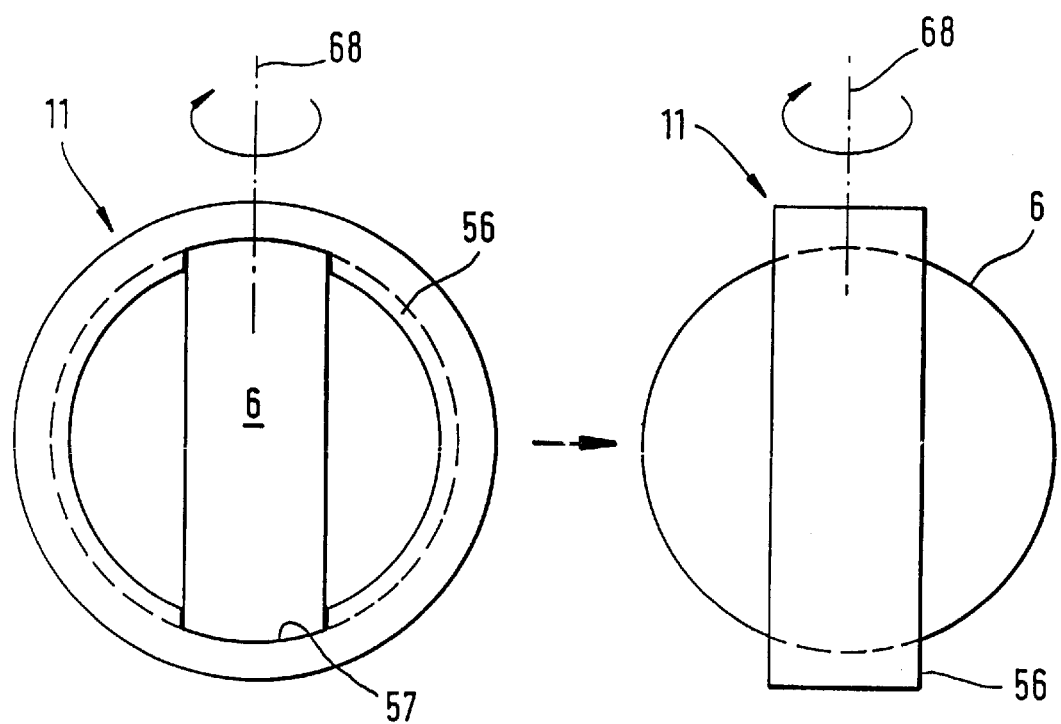
Fig. 18                Fig. 19

5,769,851

EXTERNAL FIXATOR

This application is a continuation of application Ser. No. 08/519,586 filed Aug. 25, 1995, now abandoned, the foreign priority of which is German App. #P4431525.2, filed Sep. 5, 1994 and German Application #19528839.4, filed Aug. 5, 1995.

FIELD OF THE INVENTION

The invention relates to an external fixator or a splint (hereinafter referred to as a splint) with a carrier on which at least two fastening devices are arranged to receive at least one bone screw receiving part. The bone screw receiving part holds at least one bone screw and is axially and/or radially adjustable and can be locked on the fastening device in various positions or arranged so that it can be fixed in its position. The fastening devices can be affixed onto the carrier by means of at least one locking part in order to prevent rotation and axial shifting. The bone screw receiving part can be affixed by means of at least a second locking part on a ball-and-socket joint in any desired position, whereby this joint is integrated with the fastening device or else firmly attached to it directly or indirectly.

BACKGROUND OF THE INVENTION

In general, splints are well known for use in stabilizing fractures, multiple fragment fractures or for distraction and compression treatments. Generally, they consist of a central element arranged on a threaded rod onto which at least two bone screws are attached by means of bone screw clamping jaws. In addition to the carrier, the rod having a thread also has two other bone screw clamping jaws, whereby at least one clamping jaw is provided with a ball-and-socket joint so that at least two bone screws can be adjusted with respect to the other bone screws. The individual clamping jaws can be adjusted by means of an adjusting nut which, for this purpose, is rotated on the rod in the appropriate direction in order to thus move two bone screw clamping jaws towards each other or away from each other which are arranged at a certain distance from each other. Such an adjustment of the bone screw clamping jaws is very time consuming. Moreover, the individual bone screws are not easy to adjust in the case of multiple fragment fractures to the individual bone fragments.

Accordingly, the objective of the invention is to create a splint of the type described above in such a way that a fast adaptation of the splint or of the appertaining clamping jaw which holds the bone screws to the repositioning bone part is possible with just a few movements.

SUMMARY OF THE INVENTION

This objective is achieved according to the invention in that the splint is provided with a carrier on which at least two fastening devices are arranged to receive at least one bone screw receiving part. The bone screw receiving part holds at least one bone screw and is axially and/or radially adjustable and can be locked on the fastening device in various positions or arranged so that it can be fixed in its position. The fastening devices can be affixed onto the carrier by means of at least one locking part in order to prevent rotation and axial shifting, and the bone screw receiving part can be affixed by means of at least a second locking part on a ball-and-socket joint in any desired position. This joint is integrated with the fastening device or else firmly attached to it directly or indirectly. As a result, the splint is very easy to handle and the bone screws can be adjusted in any desired position without the need for several movements to do this. Since the fastening device can also be secured onto the carrier by means of at least one locking part in order to prevent rotation and, at the same time, also to prevent axial shifting, by loosening just the receiving part, the position of the ball-and-socket joint is not simultaneously affected. If the ball-and-socket joint, however, is also supposed to be slid in the axial direction, then the rotation prevention part assures that no pivoting of the bone screws occurs but rather that they maintain their relative position.

For this purpose, it is advantageous for the fastening device to have this locking part and to be connected permanently and/or detachably with the axially and/or radially securable ball-and-socket joint on which the bone screw receiving part, that can be moved in all directions, is positioned. Since the device consists of two ball-and-socket joints arranged so as to be adjustable in all directions, it is easily possible to optimally adjust the bone screws, even in case of very complicated fractures. The use of ball-and-socket joints assures that the two bone screw clamping jaws, which are positioned at a certain distance from each other, can be slid lengthwise with great variability. The adjustability of the two ball-and-socket joints allows for a very great length variation, as well as a very rapid repositioning due to the fast sliding of the ball-and-socket joints on the carrier.

An additional possibility on the basis of another embodiment of the splint according to the invention is for the carrier to have a locking device extending in the axial direction of the carrier by means of which the ball-and-socket joint can be guided in the axial direction, can be locked and/or can be secured on the carrier to prevent rotation around a lengthwise axis of the carrier, as well as for the carrier to be designed as a rod and to have a rotation prevention part designed as a locking device for the ball-and-socket joint or a contact surface or a groove.

It is also advantageous for the ball-and-socket joint and/or the rod to have a groove to receive the intermediate element designed as a spring, by means of which it is possible to establish a radial attachment between the ball-and-socket joint and the rod, whereby an adjustment of the ball-and-socket joint in the axial direction of the rod is permissible. As a result, rotation of the ball-and-socket joint is prevented. It is also advantageous for the intermediate element to have a fastening element on at least one of its ends that establishes a clamping connection between the ball-and-socket joint and the rod. Due to the simple axial adjustment of the ball-and-socket joint on the rod, the lengthwise dynamics can be individually dosed. Moreover, the pivoting radius of the individual bone screws is not restricted by the use of ball-and-socket joints, and consequently the greatest possible flexibility in the positioning of the bone screws is assured.

With the present invention, it is of special importance for the intermediate element to have a fastening element on each of its opposite ends, so as to create a clamping connection between the ball-and-socket joint and the rod, and for the fastening element of the intermediate element to be made of an annular part that can be affixed on the rod and on the intermediate element.

Furthermore, it is advantageous for the fastening element of the intermediate element to have a bore to receive a fastening screw which presses a clamping part that is firmly positioned on the intermediate element against the surface of the rod and which secures the ball-and-socket joint against axial shifting or rotation.

For this purpose, it is advantageous for the clamping part to be firmly positioned on the two opposite ends of the intermediate element. Since the intermediate element is equipped with one fastening element to receive the bone screws, before attaching the fastening element, it is possible to secure the bone screw clamping jaw onto the ball-and-socket joint in any desired position by means of the connection element, so that as a result, an optimal adaptation of the bone screws to the individual, differently positioned bone parts is possible.

It is also advantageous for the clamping part to have a smooth, flat clamping surface that can be pressed against the surface of the rod as well as an indentation to receive the fastening screw.

In another embodiment of the invention, it is advantageous for the clamping part and/or another adjustment element to have a thread in its bore that can be screwed onto a thread of the rod. Since the clamping surface of the clamping part can be pressed against the surface of the rod, the surface pressure of the rod is kept low, thus largely avoiding notching of the clamping part, so that it can be used for a long time without being damaged. By means of the individual fastening screws that can be screwed into the bore of the fastening element or of the annular part and that exert an action on the surface of the rod via the clamping part, it is likewise assured that no damage occurs to the surface of the rod.

Moreover, it is advantageous for a measuring part to be associated with the adjustment element and for the adjustment element to be able to be pressed against the ball-and-socket joint or against the fastening element associated with the ball-and-socket joint. By using the adjustment element that can be pressed against the surface of the ball-and-socket joint or of the fastening element, the ball-and-socket joint can be adjusted precisely within millimeters in case of distraction or compression treatments. For example, it is possible for patients themselves to actuate the splint after surgery. In order to do so, for example, a 1 mm distraction is effectuated by rotating the adjustment element on the rod. Due to the great stability of the splint according to the invention, the patient can easily subject the affected leg to mild stress after a relatively short time.

Furthermore, with the splint, pseudoarthroses can be compressed and distracted. As a result, unilateral fragment shifting is also possible over large distances. Moreover, due to the universal adaptation of the ball-and-socket joints, the splint offers the possibility of simultaneous axis correction as well as simultaneous lengthwise compensation.

For this purpose, it is advantageous for the ball-and-socket joint to have a convex outer surface on which a connection element which receives the bone screw is supported so that it can be adjusted and pivoted in all directions.

It is also advantageous for the connection element to be annular and to be slit or divided on at least one side, and for it to have two clamping jaws which are arranged at a certain distance from each other with bores arranged coaxially with respect to each other, of which at least one is designed as a threaded bore for receiving a clamp screw, and for a carrier for receiving the bone screw receiving part to be on the side opposite from the clamping jaws. By using the clamping jaws of the connection element, after adjusting the connection element on the ball-and-socket joint in all directions, it is possible to rapidly affix or lock the bone screw clamping jaws within a short period of time and without much effort.

An essential advantageous embodiment is achieved in that the bone screw receiving part is supported on the carrier in such a way that it cannot rotate.

In another embodiment of the invention, it is advantageous for the bone screw receiving part to be supported on the carrier so that it can rotate and be fastened in various positions. Due to the pivoting support of the bone screw receiving part on the ball-and-socket joint, an additional adaptation of the individual bone screws is possible, if this is desired, depending on the design of the splint.

Moreover, it is advantageous for each bone screw receiving part to have one or more bone screws and for the clamping jaw part or the bone screw receiving part to have an opening or a bore into which a neck of the bone screw receiving part or of the connection element can be inserted and secured.

Furthermore, it is advantageous for the cylindrical neck to be designed as a pivoting support or as a fixed support. If, for example, the bone screw clamping jaw is to be screwed onto the cylindrical neck, then it can be designed as a pivoting support and also offer the possibility to lock the bone screw clamping jaws onto the pivoting support. Furthermore, the possibility also exists to design the cylindrical neck of the connection element as a fixed support so that the bone screw clamping jaws cannot be adjusted any further relative to the neck.

It is especially advantageous for a part of the fastening device, which is held in the groove or is present across from the contact surface, to be at a distance from the surface of the groove or of the contact surface when the fastening device is in the built-in position and for the clamping surface of the fastening device to be outside of the bore of the ball-and-socket joint.

Furthermore, it is advantageous for the clamping surface to be smaller than the other surface of the fastening device that is located adjacent to the clamping surface and for the fastening device to be arranged at a distance from the surface of the groove when the fastening device is positioned on the carrier and for the rod and/or the bone screws to be designed so as to be variable in length.

Due to the gap formed between the surface of the groove and the opposite surface of the fastening device, even with a highly accurate fit, a good possibility for adjusting the adjustment device is assured, even when the carrier is exposed to bending loads. Therefore, for the fastening of the ball-and-socket joint, a small clamping surface is adequate while the other part of the inner surface of the fastening device is positioned contact-free in the groove, that is to say, it does not function as a clamping surface. Here it is advantageous for the clamping surface of the fastening device to be outside of the bore of the ball-and-socket joint.

Moreover, it is advantageous for at least one ball-and-socket joint jaw to consist of two half-shells which are connected to each other on one side via a joint and on the other side via a clamping screw. This makes it possible to place the ball-and-socket joint jaw onto the carrier sideways, even when the splint is already in use and an axial installation of the ball-and-socket joint jaw is no longer possible.

Another possibility according to an embodiment of the device according to the invention is for the fastening device having the ball-and-socket joint to have two or more fastening screws. In this manner, the fastening screws can also be used for other purposes, for example, in order to add an extender onto the fastening screws.

In another embodiment of the invention, it is advantageous for a neck intended for receiving the locking part or the fastening screw to be attached in one piece to the ball-and-socket joint. This further improves the handling involved in adjusting the ball-and-socket joint.

According to a preferred embodiment of the solution according to the invention, on each side of the ball-andsocket joint, there are necks designed as one piece for receiving at least one locking part or at least one fastening screw. As a result, the first fastening screw can be used to fasten one neck to the carrier device and the second neck with the associated fastening screw can be used to receive the extender.

It is of special importance for the present invention for the neck to be provided with one or more fastening screws.

In conjunction with the design and arrangement according to the invention, it is advantageous that, between two connection elements or ball-and-socket joint jaws, there is an adjustment device or telescopic rod via which the ball-and-socket joint jaws can be slid axially on the carrier so that the telescopic rod can be used as an extension or contraction device.

It is also advantageous for the telescopic rod to be attached by means of clamping devices provided on the ball-and-socket joint jaws.

Moreover, it is advantageous for the telescopic rod to consist of a sleeve having a thread and a rod likewise having a thread.

For this purpose, it is advantageous for the cross section of the carrier to be circular, oval or hexagonal in shape and to have at least one rotation prevention part which prevents rotation of the ball-and-socket joint and allows an axial adjustment on the carrier device.

Moreover, it is advantageous for the carrier to be made of carbon fiber consisting of individual carbon fiber strands that can be wound in a spiral onto a core and that are compressed into any desired cross section shape after being wound onto the core.

An additional possibility according to another embodiment of the device according to the invention is for the ball-and-socket joint to consist of two bearing shell halves which can be split in the middle and on which the ball-and-socket joint jaws can be installed radially.

In this manner, it is achieved that one bearing shell half has a first flange that can be laid against the outside of the ball-and-socket joint jaw while the other bearing shell half has a second flange that can be placed in a contact position against the outside of the ball-and-socket joint jaw after the assembly of the bearing shell.

It is also advantageous for the bearing shell of the connection element to have a cutout the size of the width of the ball-and-socket joint so that, by rotating the ball-and-socket joint around its axis by 90°, the ball-and-socket joint can be inserted into the bearing shell and secured by rotating it by another 90°. For this purpose, it is important for the bearing shell to have no lateral necks and for the width of the ball-and-socket joint piece to be somewhat smaller than the width of the cutout.

Additional advantages and details of the invention are explained in the patent claims and in the description, and shown in the figures, whereby it should be pointed out that all individual features and all combinations of individual features are essential to the invention. The following is shown in the figures:

DESCRIPTION OF THE PREFERRED EMBODIMENT

The following description of the preferred embodiments are not intended to be exhaustive or to limit the application to the precise forms disclosed. Rather, they are chosen and described so that others skilled in the art might utilize their teachings.

Figure 1A:
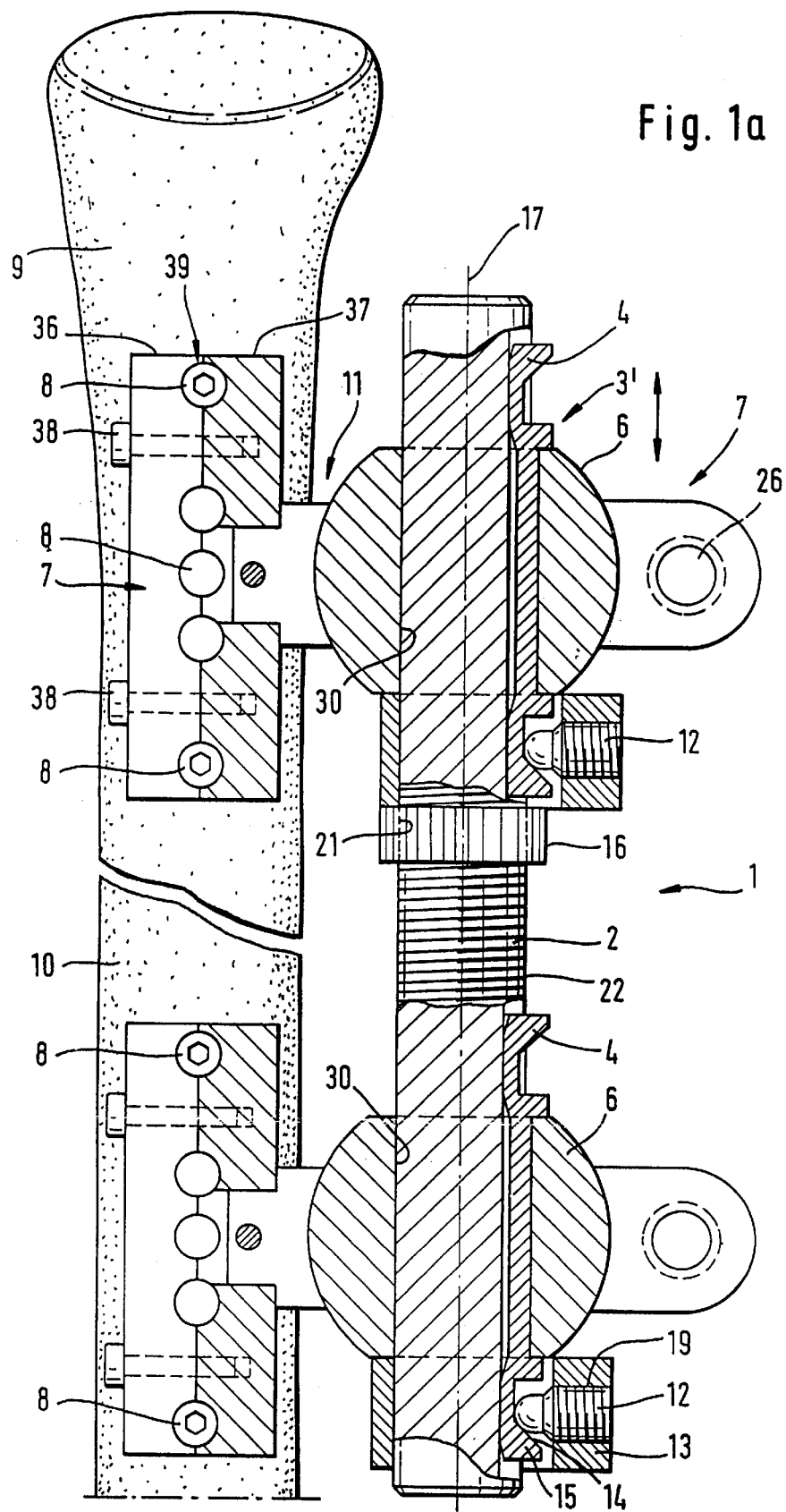
FIGS. 1a and 1b a cross sectional view of two embodiments of a splint with two ball-and-socket joints arranged on a rod in such a way that each one can receive a connection element with bone screw clamping jaws and can pivot in all directions, FIG. 2 a partial view of the ball-and-socket joint with the associated connection element for receiving a bone screw clamping jaw, FIG. 3 a front view of the ball-and-socket joint according to FIG. 2, FIG. 4 a view of the ball-and-socket joint and of the associated intermediate element designed as a spring and of the fastening device in a bottom view according to FIG. 5, FIG. 5 a cross sectional view of the ball-and-socket joint as well as of a part of the rod with the associated fastening device, FIG. 6 a cross sectional view taken along line 5—5 according to FIG. 5, FIG. 7 a cross sectional view of a second embodiment of the ball-and-socket joint with two firmly connected cylindrical necks for receiving fastening screws, FIG. 8 a cross sectional view of the second embodiment of the ball-and-socket joint with a firmly connected cylindrical neck for receiving one or more fastening screws, FIG. 9 a side view of a fastening element having a joint with a ball-and-socket joint consisting of two parts in the open position, FIG. 10 a side view of a fastening element having a joint with a ball-and-socket joint consisting of two parts in the closed position, FIG. 11 a side view of a fastening element having a joint with clamping jaw parts for receiving bone screws similar to FIG. 2, FIG. 12 a top view according to FIG. 11, FIGS. 13a and 13b a cross sectional view of a bearing shell that can be placed on the ball-and-socket joint and of a part of the connection element according to FIG. 2, FIGS. 14 and 15 two different clamping devices for an extender, FIG. 16 a cross section of the carrier according to FIG. 1b, FIG. 17 a lengthwise section of the carrier according to FIG. 1b, FIG. 18 a front view of the bearing shell of the ball-and-socket joint according to FIG. 8, FIG. 19 a side view of the bearing shell of the ball-and-socket joint according to FIGS. 8 and 18.

In the drawing, FIG. 1a uses the reference number 1 to designate a splint that can be used for fractures or fragment shifting or for distraction and compression treatments. The splint 1 consists of a carrier 2 that is designed as a rod and that can be provided with a thread 22 over part of the rod or over the entire length of the rod. The rod 2 can consist of a composite material, advantageously a carbon fiber material, so that it remains largely invisible on X-ray images. It is also possible to make the rod out of a metal alloy. The rod 2 is normally made without the thread 22 and thus has a smooth surface, so that gliding and jerk-free adjustment of the parts to be adjusted is possible. However, if the thread 22 is to be used, then the surface of the thread is treated in such a way that the gliding properties are not impaired. The carrier or the rod 2 also has a groove 3 extending in a longitudinal axis 17 of the rod 2 and this groove is designed as a rotation prevention part for a ball-and-socket joint 6. Two or more ball-and-socket joints 6 can be arranged on the rod 2 at a certain distance from each other so as to be axially slidable.

The ball-and-socket joint 6 according to FIGS. 1 through 5 consists of a sphere having a bore 30 with a convex outer surface 23 that is delimited by two opposite, parallel even end surfaces 31 or segment surfaces. The segment surface 31 intersects the longitudinal axis 17 at a right angle and is circular in shape, as can be seen in FIG. 6. The ball-and-socket joint 6 is likewise provided with a groove 18 whose cross section corresponds approximately to the groove 3 of the rod 2. If the ball-and-socket joint 6 is slid onto the rod 2, then the two grooves 3 and 18 can be aligned with each other and they then form a rectangular cross section 32. However, before the ball-and-socket joint 6 is slid onto the rod 2, the fastening device or an intermediate element 4 designed as a spring has to be inserted into the bore 30 of the ball-and-socket joint 6 and the associated groove 18. The spring or the intermediate element 4 has a clamping part 15 on each of its opposite ends which has a height H1 according to FIG. 5 that is greater than the height H2 of the middle part of the intermediate element 4. In this manner, with the appropriate fit formation with the two clamping parts 15, the intermediate element 4 can be inserted through the bore 30 and into the groove 18 of the ball-and-socket joint 6 or else simultaneously clamped tight, if appropriately small tolerances are maintained between the two opposite faces of the clamping part 15. This greatly facilitates the assembly of the ball-and-socket joint 6 in connection with the fastening device 4 on the rod 2. Between the outer surface of the rod 2 and the inner surface of the groove 4, according to FIGS. 1, 3 and 6, an interstice is formed that is marked with the reference number H3. This assures that the ball-and-socket joint 6 with the spring 4 can still be easily slid on the rod, even if the rod 2 were to bend due to an extreme load. The distance of the interstice H3 is advantageously between 0.5 and 6 mm or between 1 and 2 mm in size. After the intermediate element 4 has been inserted into the ball-and-socket joint 6, both parts can be slid onto the rod 2 so that they can then take up a position according to FIG. 1. The use of the intermediate element or of the fastening device 4 has the major advantage that, with great fitting precision, a perfect adjustment of ball-and-socket joint 6 and intermediate element 4 is also possible. For this reason, the fastening device only rests in the groove 3 with its two tongues 5 or its short clamping surfaces 20. As already mentioned, this has the great advantage that, if the carrier 2 bends slightly, clamping does not occur when the fastening device 4 is slid in the groove 3. Therefore, the middle part of the fastening device 4 has a small distance H3 from the surface of the groove 3. Here the sliding properties of the fastening device 4 are considerably improved.

The ball-and-socket joint 6 is fastened onto the rod 2 by means of the clamping part 15 and an associated fastening element 13. Two clamping parts 15 can also be used. The ball-and-socket joint 6 can be prevented from rotating by means of the groove 3, i.e. it can only be slid in the direction of the longitudinal axis 17 according to FIG. 1.

Figure 5:
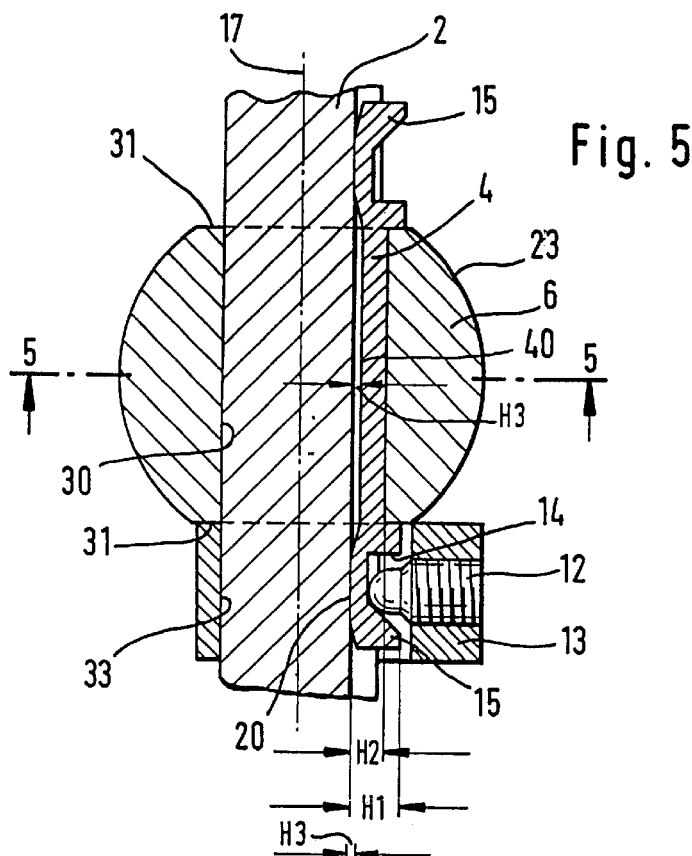
Figure 6:
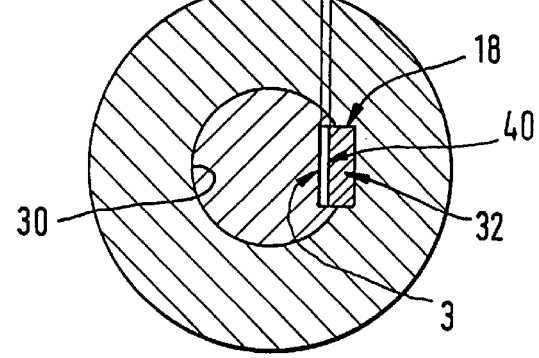

The fastening element 13 according to FIG. 5 consists of an annular part with a threaded bore for receiving a fastening screw or countersunk head screw 12 which, after it has been screwed into the bore of the fastening element 13, engages in an indentation 14. The indentation 14 is in the clamping part 15. By screwing the fastening screw 12 into the bore 19, the clamping surface 20 of the clamping part 15 is pressed against the surface of the rod 2 and thus creates a very good clamping connection between the fastening element 13, the associated ball-and-socket joint 6 and the rod 2 so that the ball-and-socket joint 6 is secured against axial shifting on the rod 2. Due to the smooth clamping surface 20 of the clamping part 15, a good surface pressure and thus clamping effect is achieved between the fastening element 13 and the rod 2 while avoiding notching effects on the surface of the rod 2.

In the embodiment according to FIG. 5, the fastening device or intermediate element 4 is provided with a clamping part 15 at each of its ends. However, it is also possible to provide an appropriate clamping part 15 on just one side of the intermediate element 4. As can also been seen from FIG. 5, a bore 33 of the fastening element 13 completely covers the clamping part 15 to be secured so that as a result, a protective effect is achieved for the clamping part 15.

Figure 2:
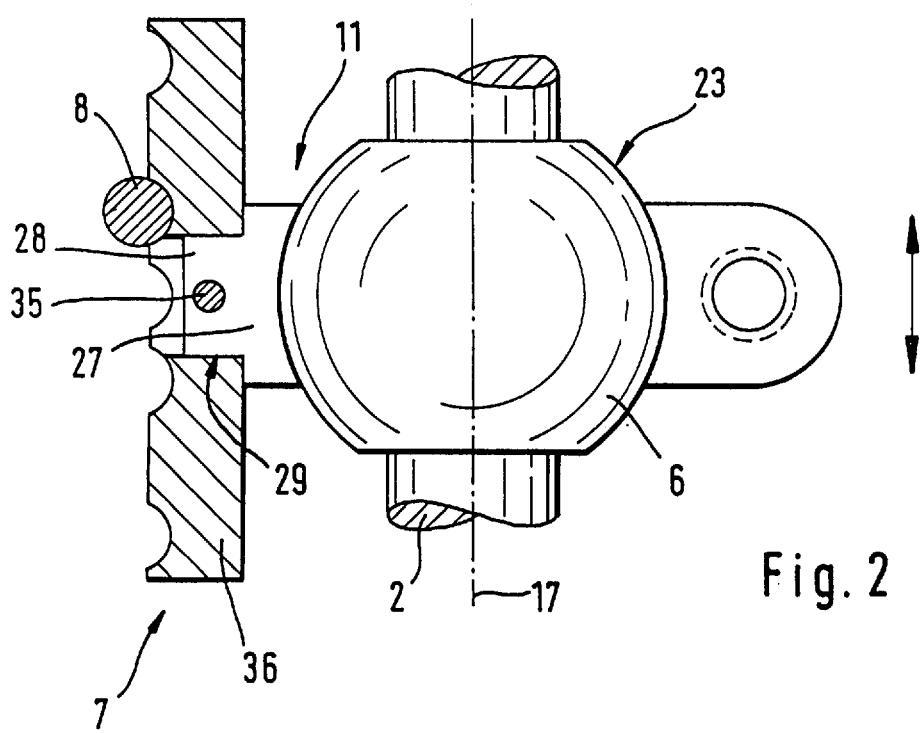
Figure 3:
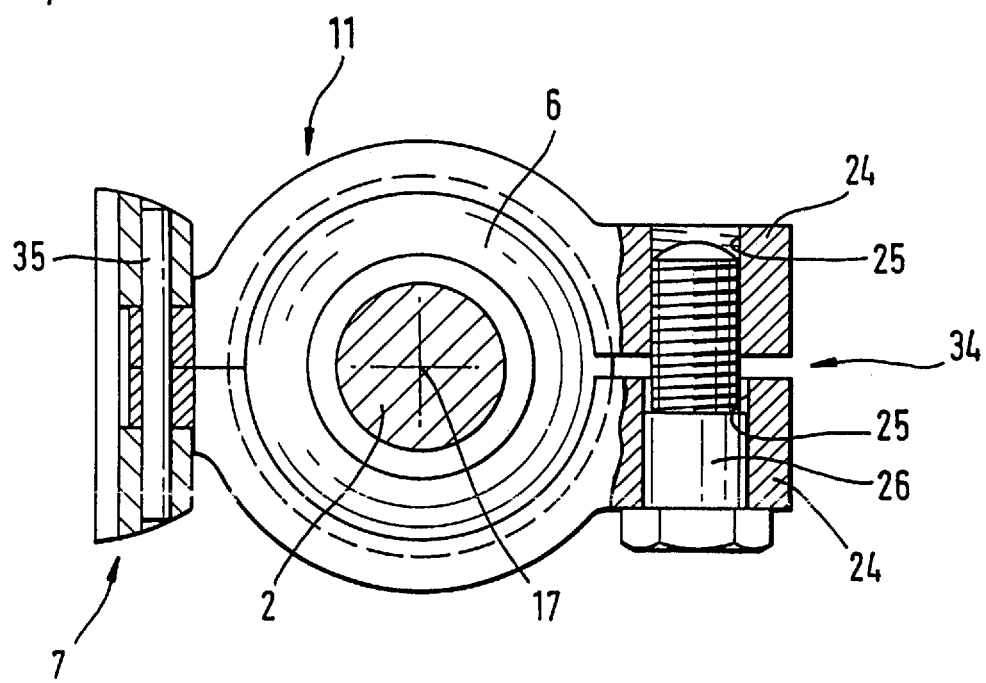
Figure 4:
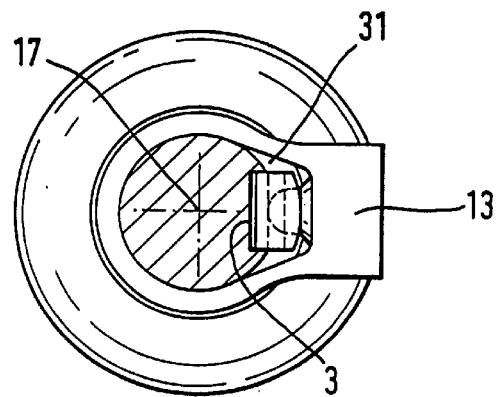

As FIGS. 2 and 3 show, the outer surface 23 of the ball-and-socket joint 6, as already mentioned, is convex in shape and serves as a contact surface of a connection element 11. The connection element 11 is ring-shaped and provided with a slit-like opening 34 on one side, thus forming two clamping jaws 24 arranged at a distance from each other, each having a bore 25. According to FIG. 3, the upper clamping jaw 24 can be provided with the threaded bore 25 into which a clamping screw 26 can be screwed so that the two clamping jaws 24 are drawn together and therefore the connection element 11 can be attached onto the outer surface 23 of the ball-and-socket joint 6. If, for example, the clamping screw 26 is loosened, then the connection element 11 can be pivoted in all directions on the outer surface 23, whereby the pivoting range of the connection element 11 is delimited by placing the bone screw receiving part 7 against the surface of the rod 2. By adjusting the connection element 11 with the associated bone screw receiving part 7, it is also possible to easily adjust bone screws 8 held in the clamping part 15 in any direction. This achieves an optimum adaptation of the bone screws 8 to the appropriate bone parts, e.g. a femur and/or tibia 9, 10, in the treatment of a fracture.

As FIG. 2 shows, across from the two clamping jaws 24, there is a carrier 27 having a cylindrical neck 28 on which the bone screw receiving part 7 is supported and safeguarded against rotation by means of a pin 35.

Depending on the embodiment, however, it is also possible to support the bone screw receiving part 7 on the carrier 27 so that it can pivot, whereby the bone screw receiving part 7 can be secured by means of a retaining ring (not shown here) on the carrier 27.

The bone screw receiving part 7 according to FIG. 1 consists of two clamping jaw parts 36 and 37 which are held together by means of screw bolts 38. For this purpose, the screw bolts 38 are screwed into appropriate bores provided in the clamping jaw parts 36 and 37. Each clamping jaw part 36, 37 has semicircular indentations which, when the two clamping jaw parts 36 and 37 are joined, form a cylindrical opening 39 in which the bone screws 8 can be adjustably received and clamped by means of the screw bolts 38.

In the embodiment according to FIG. 1, there are only two ball-and-socket joints 6 arranged at a certain distance from each other on the rod 2. However, in the case of multiple fractures, it is also possible to place several ball-and-socket joints 6 on the rod 2 and to lock them in place as described.

In the embodiment according to FIG. 2, a bore 29 of the clamping jaw part 36 is shaped cylindrically, especially when the neck is to be designed as a pivoting support. Of course, it is also possible to design the carrier 27 and the associated neck 28 to be rectangular in order to thus prevent rotation of the carrier 27 with respect to the bone screw receiving part 7.

According to FIG. 1, in addition to the fastening element 13, there can also be another adjustment element 16 provided with a bore 25 that is to be used as an adjustment screw for the fine adjustment of the ball-and-socket joint 6 on the rod 2, especially when the splint is to be used for distraction or compression treatments. The adjustment element 16 can be provided with a thread 21 having a slight pitch in order for it to be screwed onto the rod 2 having a thread 22 so that, for example, when the adjustment element 16 is turned once, the ball element on the rod 2 is adjusted by 1 mm. In this manner, it is possible for patients to actuate the splint themselves after surgery so as to influence the distraction. They can easily adjust the adjustment screw 1 mm per day.

The splint 1 referred to in the application can be designated as a holding device or external splint for the treatment of bone diseases or bone fractures. Moreover, it can be advantageous if the external splint is also designed as a one-sided (according to FIG. 1) or else a two-sided external splint. It is also especially advantageous for the rod 2 and/or the bone screws 8 to be designed so that their length can be changed.

Figure 1B:
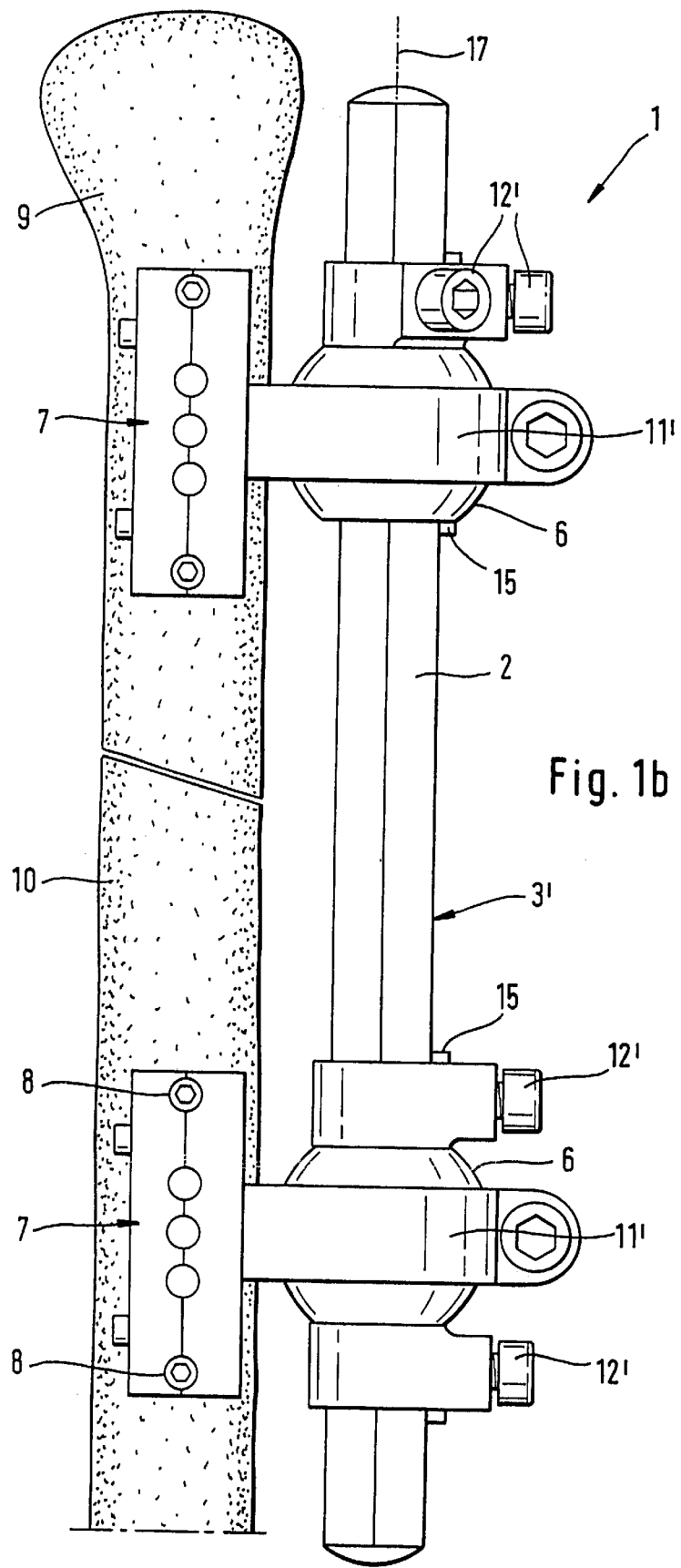

In the drawing, FIG. 1b uses reference number 1 to designate a second embodiment of a splint that can be used to treat fractures or fragment shifting or for distraction and compression treatments. The splint 1 consists of the carrier 2 that is designed as a rod and whose cross section can be either oval, triangular, rectangular or especially hexagonal in shape over part of the rod or over the entire length of the rod. In any case, the cross section is to be shaped in such a way that the ball-and-socket joint according to FIGS. 1a, 1b, 7 and 8 cannot rotate on the carrier 2 when one of the fastening screws 12, 12' or 26 is loosened.

For this purpose, the carrier 2 has a rotation prevention part that is made as a locking device for the ball-and-socket joint 6 and that is designed either as a groove or as a contact surface 3 according to FIG. 1a(see FIG. 1a) or only as a contact surface 3' (see FIG. 1b).

The rod 2 can consist of a composite material, advantageously a carbon fiber material, so that it remains largely invisible on X-ray images. It is also possible to make the rod out of a metal alloy or of a rustproof metal, for example, titanium or, for weight reasons, aluminum. The rod 2 according to FIG. 1b is designed without a thread 22 and therefore has a smooth surface with at least one contact surface 3', so that gliding and jerk-free adjustment of the parts to be adjusted is possible. The carrier 2 consists of a hexagonal element (FIG. 16) that is made of carbon fiber and is manufactured of individual carbon fiber strands 48.

In order to make the rod 2, the carbon fiber strands 48 are wound in a spiral onto a core (not shown on the drawing) which is only needed for the winding procedure, and after the winding procedure, these strands are pressed into a permanent cross-section shape and then pulled off the core (not shown here). This ensures that the surfaces of the individual strands 69 are not damaged or cut when the hexagonal shape is made.

The carrier or rod 2 has at least one contact surface 3' and, according to FIG. 16, six contact surfaces extending in the direction of the longitudinal axis 17 (FIG. 1a) which, individually or jointly, serve to prevent rotation of the ball-and-socket joint 6 when one of the adjustment screws 12', 26 is loosened.

Two or more ball-and-socket joints 6 according to FIG. 1a or 1b, or FIGS. 8 through 10 can be arranged at a certain distance from each other on the rod 2 so as to be able to slide axially.

Figure 7:
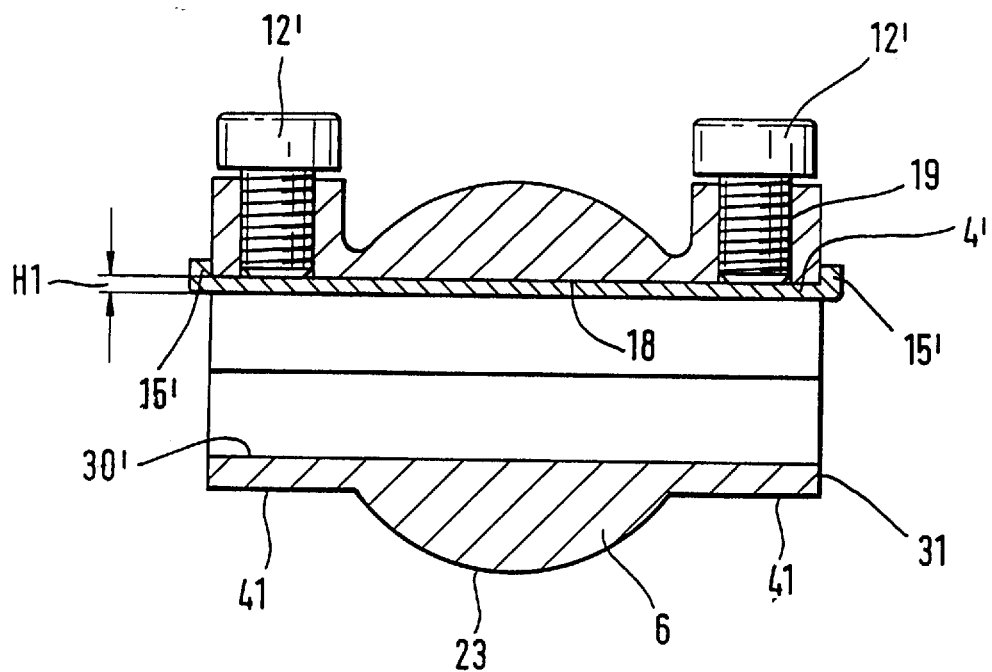
Figure 8:
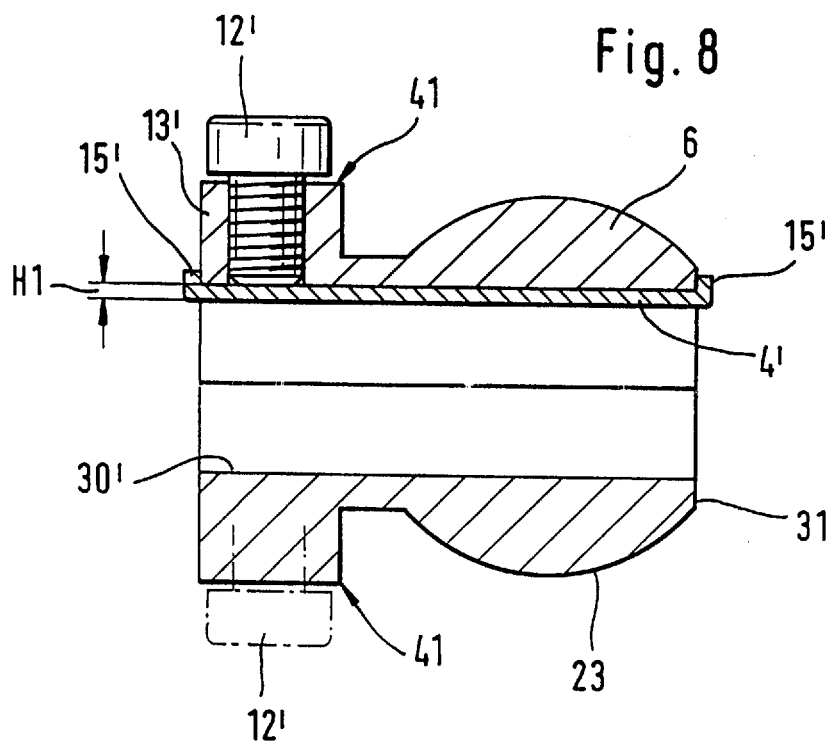

According to FIG. 8, the ball-and-socket joint 6 consists of a ball 6 having a hexagonal bore 30' and a convex outer surface 23 that is delimited by two opposite, parallel necks 41 (FIG. 7), which can be cylindrical or else can have a different cross section similar to carrier 2.

According to FIG. 8, only one neck 41 is arranged in one piece on the ball-and-socket joint 6 for receiving the locking part or the fastening screw 12'.

If, as is explained later on (FIGS. 18, 19), the ball-and-socket joint 6 is slid laterally into the connection element 11, then the neck 41 can also be detachably screwed, clamped or connected via additional connection elements to the ball-and-socket joint 6.

The necks 41 according to FIG. 7 and FIG. 8 serve to receive at least one, two or more fastening screws 12'.

The ball-and-socket joint 6 is likewise provided with a groove 18 whose cross section corresponds approximately to the groove 3 or the contact surface 31 of the rod 2. When the ball-and-socket joint 6 is slid onto the rod 2, then the two contact surfaces 3 and 18 can be aligned with each other, thus forming a surface whose cross section is a rectangular surface. However, before the ball-and-socket joint 6 is slid onto the rod 2, the fastening device or the intermediate element 4' designed as a spring has to be inserted into the bore 30' of the ball-and-socket joint 6. At each of its two opposite ends, the spring or intermediate element 4' has a hook element 15' according to FIG. 8 that is placed against the surface 31 of the ball-and-socket joint 6 when it is inserted into the bore 30'.

The middle part of the fastening device 4' can likewise have a smaller distance H3 from the surface of the contact surface 3, similar to FIG. 6. This considerably improves the sliding properties of the fastening device 4'.

The connection element 11 and 11' shown in FIGS. 9 through 12, similar to FIG. 3, is split on at least one side and provided with a slit-shaped opening 34.

Figure 9:
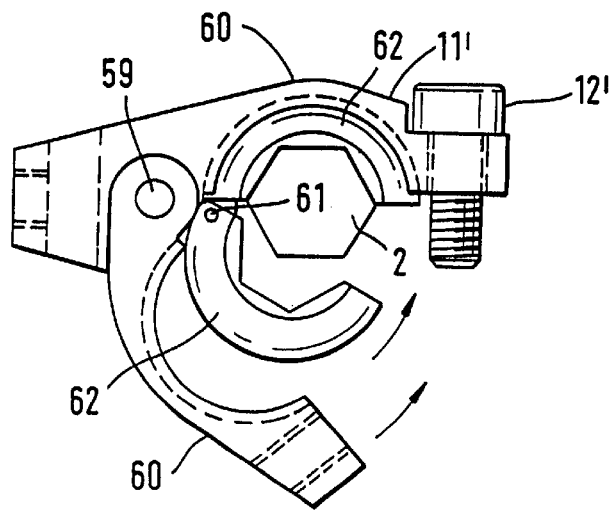
Figure 10:
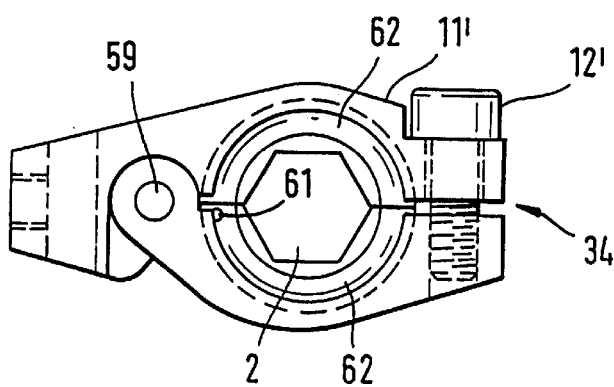
Figure 11:
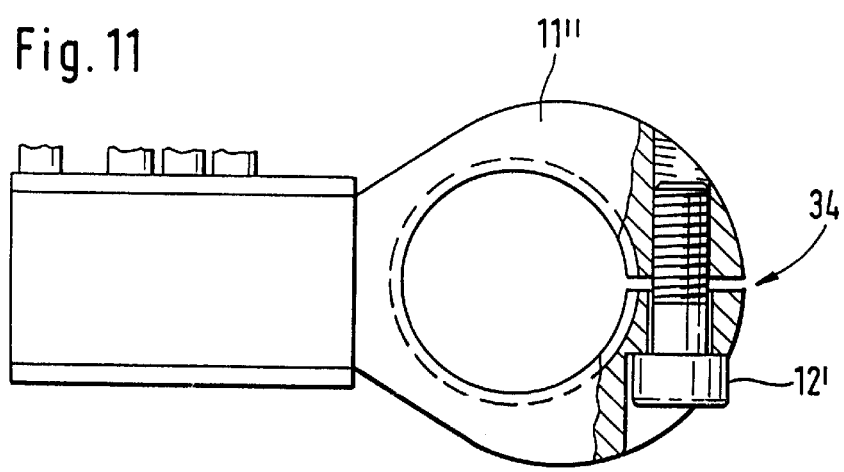
Figure 12:
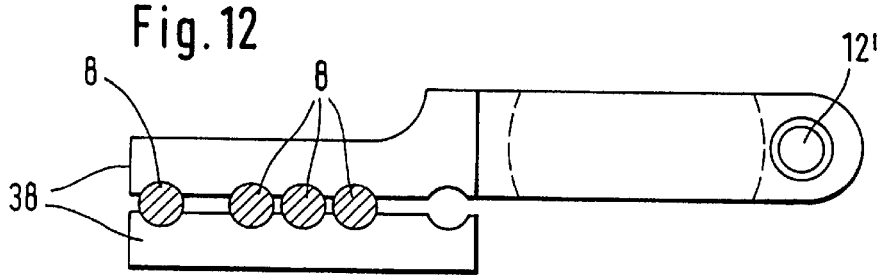

The connection element 11' shown in FIGS. 9 and 10 consists of two bearing shells 60 which are connected to each other by means of a hinge bolt 59 and which can likewise be joined and tightly connected to each other by means of the fastening screw 12'. In this manner, it is also possible to subsequently install the connection element IV on the side of the carrier 2. For this purpose, the ball-and-socket joint 6 is made up of two ball-and-socket joint parts 62 connected to each other by means of a hinge bolt 61, and these parts can be installed laterally on the carrier 2 in the position according to FIG. 9 and then secured by means of the connection element 11' and the fastening screw 12'.

Figures 13A, 13B:
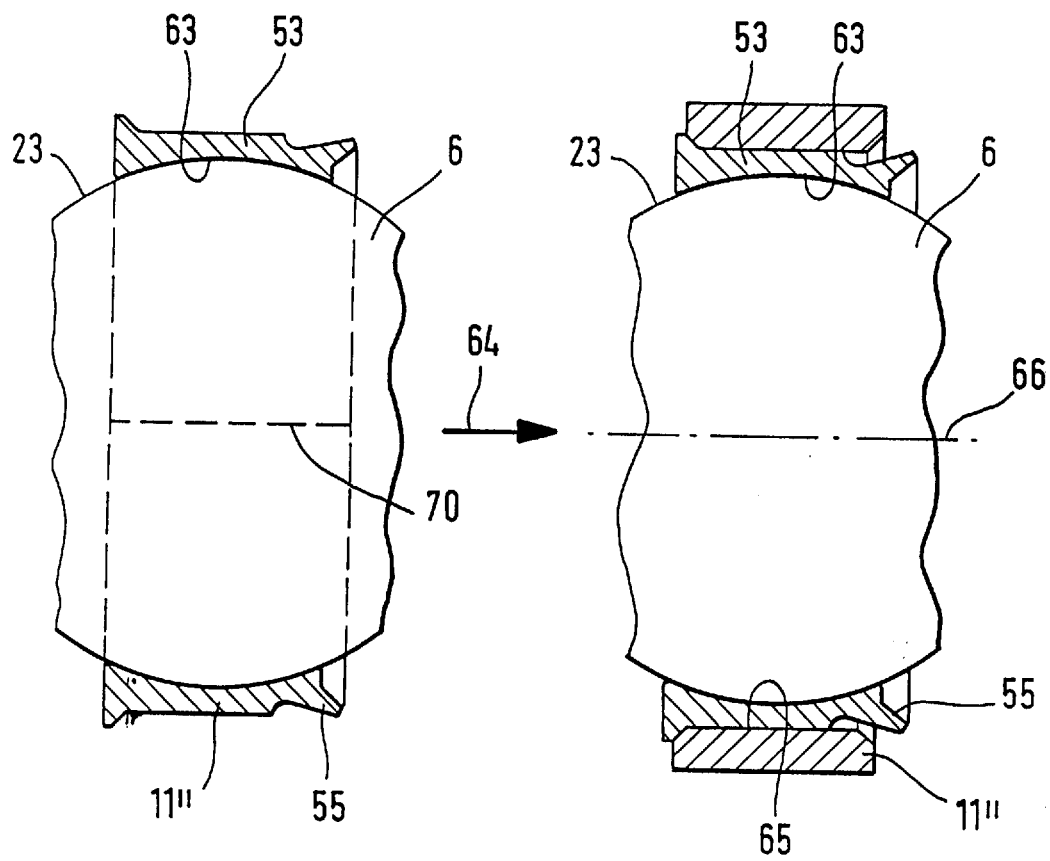

As can be seen in FIGS. 13a and 13b, a bearing shell 53 can be installed on the outer surface 23 of the ball-and-socket joint 6 and its inner surface 63 is matched to the outer surface 23 of the ball-and-socket joint 6. The bearing shell 53 can be split in the middle at 70 and be joined after the placement of the bearing shells 53. When the two bearing shells 53 according to FIG. 13b have been secured on the ball-and-socket joint 6, they are inserted together along arrow 64 into the bore 65 of the connection element 11' until the flange 54 comes to lie against the face of the connection element 11'. Then the second flange 55, which forms an angle ranging from 30° to 60°, especially 45°, with respect to the middle axis 66, is bent, so that its entire surface likewise comes to lie against the face of the connection element 11", thereby securing the ball-and-socket joint 6 in the bore 65 of the connection element 11".

It is also possible to make the bearing shell so that it consists of one single piece and is not deformable, in order to slide it over the ball-and-socket joint 6.

On the basis of another embodiment according to FIGS. 18 and 19, the bearing shell 56 of the connection element 11 can have a cutout 57 the size of the width of the ball-and-socket joint 6 so that, by rotating the ball-and-socket joint 6 by 90° around its middle axis 68, it can be inserted through the cutout 57 into the bearing shell 56, and by once more rotating the ball-and-socket joint 6 by another 90° according to FIG. 18, it can be secured in the annular gap of the bearing shell 56.

Between two connection elements 11 or 11', according to FIGS. 1b and 15, an adjustment device or telescopic rod 42 can be provided that consists of a sleeve 45 having an inner thread 44 and a rod 46 likewise having a thread 47 which, upon rotation, effectuates a change of the distance between the fastening screws 12' and the connection elements 11.

According to FIGS. 14 and 15, the rod 42 is held in a clamping device 43 that is adjusted by means of the adjustment screw 12', thus securing and clamping or else releasing the rod 46 when a change of the distance is to be made between two fixed points such as, for example, the connection elements 11.

According to FIG. 14, one end of the telescopic rod 42 can have a pivoting support 70 that is secured by means of two securing rings 71 that lie against both sides of the connection element 11 on the telescopic rod 42 in the axial direction, but this pivoting support 70 allows a rotation of at least one part or of the rod 46 so that, by rotating the rod 46, the sleeve 45 can be adjusted in the axial direction on the rod 46, thus bringing about a change of the distance between two ball-and-socket joints 6.

It is also possible that, instead of the left-hand securing ring, there can be an adjustment ring having a thread or a lock nut 71 that brings about an adjustment of the one ball-and-socket 6 vis-a-vis the other ball-and-socket joint 6 by means of a rotating screw head 72 provided on the end of the rod 46. The screw head 72 then replaces the second, right-hand securing ring. The right-hand end of the rod 46 is then supported in a bore provided in the neck 41.

The clamping device 43 shown in FIG. 15 is used when, for example, the left-hand ball-and-socket joint 6, according to FIG. 14, is not present. In this case, the right-hand end can rest directly on the carrier 2 over the clamping device 43. Then one end of the rod 46 is attached to the clamping device 43 by means of the screw 12' and a bearing lug (not shown here), similar to FIG. 14.

It should be understood that the invention should not be limited to the precise forms disclosed, but may be modified within the keeping of the appended claims.

I claim:

1. A splint (1) with a carrier (2) on which at least two fastening devices (4) are arranged to receive at least one bone screw receiving part (7), the bone screw receiving part holds at least one bone screw (8) and is axially and radially adjustable and can be locked on the fastening device (4) in various positions, whereby the fastening devices (4) can be affixed onto the carrier (2) by means of at least one locking part (12), said carrier includes at least one flat surface (31) engaged by the at least two fastening devices (4) in order to prevent rotation and axial shifting, the bone screw receiving part (7) can be affixed by means of at least a second locking part (26) on a ball-and-socket joint (6) in any desired position, whereby the ball-and-socket joint is firmly attached to the fastening device, wherein, the ball-and-socket joint (6) and the rod (2) have cooperating grooves (3, 18) to receive an intermediate element (4) designed as a spring, the intermediate element constituting means for preventing rotation between the ball-and-socket joint (6) and the rod (2), whereby an adjustment of the ball-and-socket joint (6) in an axial direction of the rod (2) is permissible.

2. The splint of claim 1 wherein the carrier (2) has a locking device (4, 15, 12, 13, 16, 19) extending in an axial direction of the carrier (2) by means of which the ball-and-socket joint (6) can be guided onto the carrier (2) in the axial direction and can be locked and secured on the carrier against rotation around a lengthwise axis (17) of the carrier (2).

3. The splint of claim 1 wherein the intermediate element (4) is elongated and defines two opposing ends, the intermediate element has a fastening element (13) on at least one of its ends that provides a clamping connection between the ball-and-socket joint (6) and the rod (2).

4. The splint of claim 3 wherein the intermediate element (4) has a fastening element (13) on each of its opposite ends, so as to create a clamping connection between the ball-and-socket joint (6) and the rod (2).

5. The splint of claim 4 wherein the fastening element (13) of the intermediate element (4) is made of an annular part that can be affixed on the rod (2) and on the intermediate element (4).

6. The splint of claim 3 wherein the fastening element (13) of the intermediate element (4) has a bore to receive a fastening screw (12) which presses a clamping part (15) that is firmly positioned on the intermediate element (4) against the surface of the rod (2) and which secures the ball-and-socket joint (6) against axial shifting or rotation.

7. The splint of claim 6 wherein the clamping part (15) is firmly positioned on the two opposite ends of the intermediate element (4).

8. The splint of claim 6 wherein the clamping part (15) has a smooth, flat clamping surface (20) that can be pressed against the surface of the rod (2).

9. The splint of claim 8 wherein the clamping surface (20) of the fastening device (4) extends outwardly from the ball-and-socket joint (6).

10. The splint of claim 6 wherein the clamping part (15) has an indentation (14) to receive the fastening screw (12).

11. The splint of claim 1 wherein the ball-and-socket joint (6) has a convex outer surface (23) on which a connection element (11) which receives the bone screw (8) is supported so that it can be pivoted in all directions.

12. The splint of claim 11 wherein the connection element (11, 11') is annular and is slit or divided on at least one side.

13. The splint of claim 12 wherein the connection element (11) is annular and has two clamping jaws (24) which are arranged at a certain distance from each other with bores (25) arranged coaxially with respect to each other, at least one bore is designed as a threaded bore for receiving a clamp screw (26).

14. The splint of claim 13 wherein a carrier (27) for receiving the bone screwing receiving part (7) is on a side opposite from the clamping jaws (24).

15. The splint of claim 14 wherein the bone screw receiving part is supported on the carrier (27) in such a way that it cannot rotate.

16. The splint of claim 15 wherein the bone screw receiving part (7) is supported on the carrier (27) so that it can rotate and be fastened in various positions.

17. The splint of claim 16 wherein the bone screw receiving part (7) has an opening (29) into which either a neck (28) of the bone screw receiving part (7) and of the connection element (11) can be inserted and secured.

18. The splint of claim 1 wherein a part of the fastening device (4) held in a groove (3) in the rod and is spaced from a surface of the groove a distance H3.

19. The splint of claim 1 wherein the ball-and-socket joint (11") consists of two half-shells which are connected to each other on one side via a joint and on the other side via a clamping screw.

20. The splint of claim 1 and including an adjustment device carried on the carrier and interconnecting the two connection elements whereby the connection elements can be axially shifted on the carrier.

21. The splint of claim 1 wherein the carrier (2) is made of carbon fiber consisting of individual carbon fiber strands that can be wound in a spiral onto a core and that are compressed into any desired cross section shape after being wound onto the core.

22. The splint of claim 1 wherein the fastening element (13) of the intermediate element (4) is made of an annular part that can be affixed on the rod (2) and on the intermediate element (4).

23. A splint with an elongated carrier (2) having at least two fastening devices connected thereto, the fastening devices being adapted to receive at least one bone screw, the elongated carrier including an elongated groove which is aligned with an elongated groove formed in each fastening device, the elongated groove having a bottom surface an intermediate element (4) being positioned within the aligned grooves of the carrier and fastening device for preventing rotation of the fastening device relative to the carrier, the intermediate member having a longitudinal end which contacts a bottom surface of the elongated groove and a middle portion which is spaced from the bottom surface of the groove.

24. The splint of claim 23 wherein the intermediate portion extends outwardly of the fastening devices and is configured for contact with a clamping screw.

25. A splint with a carrier on which at least two fastening devices are arranged to receive at least one bone screw receiving part, the bone screw receiving part holds at least one bone screw and is adjustable in various positions, whereby the fastening devices are composed of at least one ball-and-socket joint carried on the carrier for axial movement and a intermediate element whereby the intermediate element of the fastening device includes at least one interior flat surface which cooperates with a flat exterior surface of the carrier to prevent the fastening device from rotating relative to the carrier, a locking part carried by the intermediate element to lock the fastening device to the carrier and thereby preventing movement of the fastening device relative to the carrier.

26. The splint of claim 25 wherein the ball-and-socket joint and intermediate element integrally formed.

27. The splint of claim 25 wherein the fastening socket portion of the ball-and-socket portion of the fastening device includes first and second portions connected about the ball portion of the ball-and-socket joint, wherein said ball portion of the ball-and-socket joint includes first and second halves hinged together such that the first and second halves of the ball portion can be hinged open to position the ball portion on the carrier.

28. A splint with a carrier on which at least two fastening devices are arranged to receive at least one bone screw receiving part, the bone screw receiving part holds at least one bone screw and is axially and radially adjustable and can be locked on the fastening device in various positions, the fastening devices each including a ball-and-socket joint wherein the ball portion of the ball-and-socket joint is formed from first and second ball portions hinged together such that the ball portion can be opened for placement on the carrier, the socket portion of the ball-and-socket joint including first and second socket portions hinged together such that the socket can be opened and placed around the ball portion of the ball-and-socket joint, whereby the fastening devices can be affixed onto the carrier by means of at least one locking part, said carrier includes at least one flat surface engaged by the at least two fastening devices in order to prevent rotation and axial shifting, the bone screw receiving part can be affixed by means of at least a second locking part on a ball-and-socket joint in any desired position, whereby the ball-and-socket joint is firmly attached to the fastening device.

* * * * *